United States Patent
Schweikert et al.

(10) Patent No.: US 9,999,723 B2
(45) Date of Patent: Jun. 19, 2018

(54) HUBER NEEDLE ASSEMBLY WITH SAFETY CAPTURE DEVICE

(71) Applicant: MEDICAL COMPONENTS, INC., Harleysville, PA (US)

(72) Inventors: Timothy M. Schweikert, Levittown, PA (US); Mark S. Fisher, Sellersville, PA (US); Joshua Lee Ballard, Abington, PA (US)

(73) Assignee: Medical Components, Inc., Harleysville, PA (US)

( * ) Notice: Subject to any disclaimer, the term of this patent is extended or adjusted under 35 U.S.C. 154(b) by 661 days.

(21) Appl. No.: 14/512,086

(22) Filed: Oct. 10, 2014

(65) Prior Publication Data

US 2015/0105727 A1    Apr. 16, 2015

Related U.S. Application Data

(60) Provisional application No. 61/889,220, filed on Oct. 10, 2013.

(51) Int. Cl.
| | |
|---|---|
| *A61M 5/158* | (2006.01) |
| *A61M 5/162* | (2006.01) |
| *A61M 5/32* | (2006.01) |

(52) U.S. Cl.
CPC .......... *A61M 5/158* (2013.01); *A61M 5/1626* (2013.01); *A61M 5/3216* (2013.01); *A61M 2005/1581* (2013.01)

(58) Field of Classification Search
CPC .......... A61M 2005/1581; A61M 5/158; A61M 5/1626; A61M 5/3216
See application file for complete search history.

(56) References Cited

U.S. PATENT DOCUMENTS

| | | |
|---|---|---|
| 4,627,343 A | 12/1986 | Raines |
| 4,735,618 A | 4/1988 | Hagen |
| 4,737,144 A | 4/1988 | Choksi |
| 4,887,998 A | 12/1989 | Martin et al. |
| 4,978,344 A | 12/1990 | Dombrowski et al. |
| 5,059,180 A | 10/1991 | McLees |
| 5,171,303 A | 12/1992 | DeCamp |

(Continued)

FOREIGN PATENT DOCUMENTS

| | | |
|---|---|---|
| CN | 101415453 C6 | 4/2009 |
| EP | 1116493 | 7/2001 |

(Continued)

*Primary Examiner* — Brandy S Lee
(74) *Attorney, Agent, or Firm* — Buchanan Ingersoll & Rooney PC

(57) ABSTRACT

A Huber needle assembly with safety capture device includes at least a body, a needle, and a movable arm. The movable arm is pivotable relative to the body, and includes a capture hood at a distal end thereof. The capture hood is cylindrical, includes a perimeter side wall having an outer face and an inner face, and has open proximal end. The capture hood includes a slot through the perimeter side wall, providing access into an internal chamber defined by the perimeter side wall. The slot extends longitudinally over at least a portion of the length of the capture hood, and at least a portion of the slot has a width less than the outside diameter of the needle to capture a tip of the needle therein when the movable arm pivots to a safety-capture position.

24 Claims, 6 Drawing Sheets

(56) References Cited

U.S. PATENT DOCUMENTS

| | | | |
|---|---|---|---|
| 5,300,046 A | 4/1994 | Scarfone et al. | |
| 5,322,517 A | 6/1994 | Sircom et al. | |
| 5,328,482 A | 7/1994 | Sircom et al. | |
| 5,382,240 A | 1/1995 | Lam | |
| 5,531,704 A | 7/1996 | Knotek | |
| 5,611,781 A | 3/1997 | Sircom et al. | |
| 5,662,610 A | 9/1997 | Sircom | |
| 5,697,907 A | 12/1997 | Gaba | |
| 5,743,383 A | 4/1998 | Visconti | |
| 5,879,337 A | 3/1999 | Kuracina et al. | |
| 5,925,020 A | 7/1999 | Nestell | |
| 5,951,522 A | 9/1999 | Rosato et al. | |
| 5,951,525 A | 9/1999 | Thorne et al. | |
| 5,997,504 A | 12/1999 | Bell | |
| 6,001,080 A | 12/1999 | Kuracina et al. | |
| 6,117,108 A | 9/2000 | Woehr et al. | |
| 6,161,630 A | 12/2000 | Stump et al. | |
| 6,254,575 B1 | 7/2001 | Thorne, Jr. et al. | |
| 6,261,259 B1 | 7/2001 | Bell | |
| 6,280,420 B1 | 8/2001 | Ferguson et al. | |
| 6,287,278 B1 | 9/2001 | Woehr et al. | |
| 6,443,929 B1 | 9/2002 | Kuracina et al. | |
| 6,537,255 B1 | 3/2003 | Raines | |
| 6,592,556 B1 | 7/2003 | Thorne | |
| 6,595,955 B2 | 7/2003 | Ferguson et al. | |
| 6,613,015 B2 | 9/2003 | Sandstrom et al. | |
| 6,623,462 B2 | 9/2003 | Guzzo et al. | |
| 6,629,959 B2 | 10/2003 | Kuracina et al. | |
| 6,676,633 B2 | 1/2004 | Smith et al. | |
| 6,719,721 B1 | 4/2004 | Okazaki et al. | |
| 6,719,731 B2 | 4/2004 | Parmigiani | |
| 6,796,962 B2 | 9/2004 | Ferguson et al. | |
| 6,796,968 B2 | 9/2004 | Ferguson et al. | |
| 6,824,530 B2 | 11/2004 | Wagner et al. | |
| 6,860,871 B2 | 3/2005 | Kuracina et al. | |
| 6,878,136 B2 | 4/2005 | Fleury et al. | |
| 6,884,224 B2 | 4/2005 | Dalton | |
| 6,902,546 B2 | 6/2005 | Ferguson | |
| 6,918,894 B2 | 7/2005 | Fleury et al. | |
| 6,926,693 B2 | 8/2005 | Enns | |
| 6,932,803 B2 | 8/2005 | Newby | |
| 6,949,086 B2 | 9/2005 | Ferguson et al. | |
| 6,969,372 B1 | 11/2005 | Halseth | |
| 6,984,213 B2 | 1/2006 | Horner et al. | |
| 6,997,902 B2 | 2/2006 | Thorne et al. | |
| 7,004,927 B2 | 2/2006 | Ferguson et al. | |
| 7,008,402 B2 | 3/2006 | Ferguson et al. | |
| 7,029,461 B2 | 4/2006 | Ferguson et al. | |
| 7,097,637 B2 | 8/2006 | Triplett et al. | |
| 7,125,397 B2 | 10/2006 | Woehr et al. | |
| 7,125,398 B2 | 10/2006 | Garcia | |
| 7,144,389 B2 | 12/2006 | Ferguson et al. | |
| 7,179,244 B2 | 2/2007 | Smith et al. | |
| 7,198,618 B2 | 4/2007 | Ferguson et al. | |
| 7,214,211 B2 | 5/2007 | Woehr et al. | |
| 7,226,434 B2 | 6/2007 | Carlyon | |
| 7,264,613 B2 | 9/2007 | Woehr et al. | |
| 7,291,135 B2 | 11/2007 | Ono | |
| 7,341,573 B2 | 3/2008 | Ferguson et al. | |
| 7,347,842 B2 | 3/2008 | Thorne et al. | |
| 7,357,784 B2 | 4/2008 | Ferguson | |
| 7,413,562 B2 | 8/2008 | Ferguson et al. | |
| 7,422,573 B2 | 9/2008 | Wilkinson et al. | |
| 7,438,703 B2 | 10/2008 | Barrus et al. | |
| 7,455,664 B2 | 11/2008 | Fleury et al. | |
| 7,458,954 B2 | 12/2008 | Ferguson et al. | |
| 7,534,231 B2 | 5/2009 | Kuracina et al. | |
| 7,549,979 B2 | 6/2009 | Enns et al. | |
| 7,569,044 B2 | 8/2009 | Triplett et al. | |
| 7,608,057 B2 | 10/2009 | Woehr et al. | |
| 7,611,485 B2 | 11/2009 | Ferguson | |
| 7,611,487 B2 | 11/2009 | Woehr et al. | |
| 7,618,395 B2 | 11/2009 | Ferguson | |
| 7,625,360 B2 | 12/2009 | Woehr et al. | |
| 7,717,888 B2 | 5/2010 | Vaillancourt et al. | |
| 7,758,544 B2 | 7/2010 | Solomon et al. | |
| 7,762,992 B2 | 7/2010 | Triplett et al. | |
| 7,776,016 B1 | 8/2010 | Halseth | |
| 7,858,774 B2 | 12/2010 | Ionescu et al. | |
| 7,927,314 B2 | 4/2011 | Kuracina et al. | |
| 8,002,746 B2 | 8/2011 | Erskine | |
| 8,496,626 B2 | 7/2013 | Hiraoka et al. | |
| 8,500,703 B2 | 8/2013 | Lambert | |
| 8,574,197 B2 | 11/2013 | Halseth et al. | |
| 8,834,422 B2 | 9/2014 | Walker et al. | |
| 9,248,234 B2 | 2/2016 | Barron | |
| 2002/0099338 A1 | 7/2002 | Young | |
| 2002/0173749 A1 | 11/2002 | Wagner et al. | |
| 2003/0114797 A1 | 6/2003 | Vaillancourt et al. | |
| 2003/0163097 A1 | 8/2003 | Fleury et al. | |
| 2004/0049159 A1 | 3/2004 | Barrus et al. | |
| 2004/0082922 A1 | 4/2004 | Fleury et al. | |
| 2004/0087912 A1 | 5/2004 | Swenson | |
| 2004/0147881 A1 | 7/2004 | Hyun | |
| 2004/0167477 A1 | 8/2004 | Wilkinson et al. | |
| 2004/0220528 A1 | 11/2004 | Garcia | |
| 2004/0260250 A1* | 12/2004 | Harris | A61M 5/158 604/263 |
| 2005/0080386 A1 | 4/2005 | Reid | |
| 2005/0107748 A1* | 5/2005 | Thorne | A61M 5/158 604/263 |
| 2006/0129106 A1 | 6/2006 | Ferguson et al. | |
| 2007/0010622 A1 | 1/2007 | Naito et al. | |
| 2007/0106222 A1 | 5/2007 | Bennett | |
| 2007/0282275 A1 | 12/2007 | Ferguson et al. | |
| 2008/0097304 A1 | 4/2008 | Thorne | |
| 2008/0119795 A1 | 5/2008 | Erskine | |
| 2008/0171986 A1 | 7/2008 | Baid | |
| 2008/0208139 A1 | 8/2008 | Scheurer et al. | |
| 2008/0262434 A1 | 10/2008 | Vaillancourt | |
| 2009/0062744 A1 | 3/2009 | Weilbacher et al. | |
| 2009/0137958 A1 | 3/2009 | Erskine | |
| 2009/0163875 A1 | 6/2009 | Hiraoka et al. | |
| 2009/0249605 A1 | 10/2009 | Erskine | |
| 2010/0137815 A1 | 6/2010 | Kuracina et al. | |
| 2010/0280413 A1 | 11/2010 | Ferguson et al. | |
| 2011/0166526 A1 | 7/2011 | Kuracina et al. | |
| 2011/0220274 A1 | 9/2011 | Erskine | |
| 2012/0123332 A1 | 5/2012 | Erskine | |

FOREIGN PATENT DOCUMENTS

| | | |
|---|---|---|
| EP | 1 430 921 A2 | 6/2004 |
| EP | 2 016 964 A1 | 1/2009 |
| EP | 2 609 953 A1 | 7/2013 |
| EP | 2 827 924 A1 | 1/2015 |
| JP | 2003-275310 A2 | 9/2003 |
| JP | 2003-195227 A2 | 7/2004 |
| JP | 2004-195227 A2 | 7/2004 |
| JP | 2009-142658 A2 | 7/2009 |
| JP | 2010-207634 A2 | 9/2010 |
| JP | 2011-115615 A2 | 6/2011 |
| WO | 99/07424 A1 | 2/1999 |
| WO | 02/087672 A1 | 11/2002 |
| WO | 2005049109 A1 | 6/2005 |
| WO | 2005/120624 A1 | 12/2005 |
| WO | 2006/096633 A1 | 9/2006 |
| WO | 2006/096634 A1 | 9/2006 |
| WO | 2006/096635 A1 | 9/2006 |
| WO | 2006/096636 A1 | 9/2006 |
| WO | 2010/101573 A1 | 9/2010 |

* cited by examiner

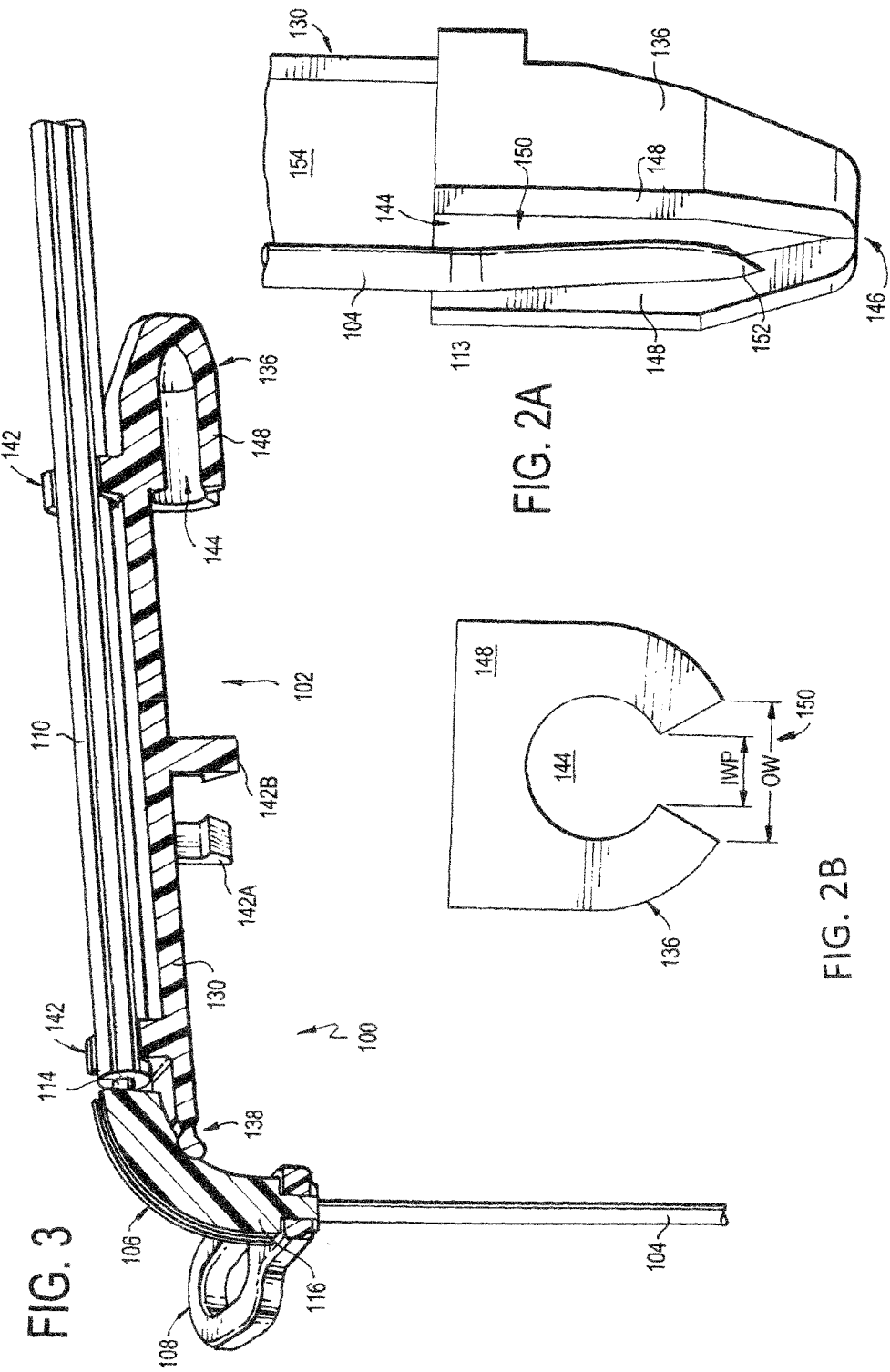

HUBER NEEDLE ASSEMBLY WITH SAFETY CAPTURE DEVICE

CROSS-REFERENCE TO RELATED APPLICATIONS

This application claims priority to U.S. Provisional Application No. 61/889,220, filed Oct. 10, 2013, the contents of which are incorporated by reference herein.

FIELD

The present invention relates to needles for subcutaneous injections. In particular, the present invention relates to Huber needles with safety capture devices.

BACKGROUND

Huber needles are widely used in hospitals and alternate care sites, and are often used in conjunction with implanted ports. Such Huber needles provide a non-coring needle that is used to administer chemotherapy, IV fluids, medications, total parenteral nutrition, or to transfuse blood products through the implanted ports. The implanted ports contain a self-sealing septum that seals around the needle, holds the needle in place, and allows for multiple accessing by a Huber needle.

The Huber needle is designed for the safety of the patient; however Huber needles can present considerable risk to the user, tuber needles, if improperly used, expose the user to bloodborne pathogens, or to the drug or medication being administered through the Huber needle. Often, two hands are required to extract the needle from the implanted port. One hand is used to stabilize the implanted port, while the other hand is used to withdraw the needle. The force required to withdraw the needle from the self-sealing septum of the implanted port can cause the needle to rebound and possibly result in needle stick injury to the user. Such a needle stick injury could transfer a blood borne pathogens such as Hepatitis or HIV, to the user. Accordingly, there exists a continuing need for Huber needles having safety features minimizing risk of injury and exposure to the user.

SUMMARY

The present invention provides a Huber needle assembly with safety capture device that minimizes the risk of injury and exposure of the needle to the user/medical practitioner. In one aspect of the invention, a Huber needle assembly with safety capture device is provided and includes a body, a needle distally extending from the body, at least one handle, a movable arm, and a capture hood. The movable arm, having distal and proximal ends, is pivotable relative to the body. The at least one handle can be fixed relative to the needle and the body.

The capture hood can reside at the distal end of the movable arm, and can be generally cylindrical about a longitudinal axis thereof. The capture hood can be further defined by a perimeter side wall residing axially about the longitudinal axis, where the perimeter side wall has an outer face and an inner face relative to the longitudinal axis. The capture hood further includes an open proximal end and a slot through the perimeter side wall. The distal end of the capture hood can be open or closed.

The slot has a depth defined by a thickness of the side wall through which the slot extends, the thickness existing between the outer face and the inner face of the side wall. In view thereof, the slot has two sides, each characterized by an edge residing along the depth (i.e., residing along the thickness (an edge) of the side wall between the outer face and the inner face of the side wall). The slot provides access into an internal cylindrical chamber of the capture hood. The internal chamber is defined at least in part by the perimeter side wall. The slot extends longitudinally over at least a portion of the length of the capture hood, through to the open proximal end of the capture hood. At least a portion of the slot has a width less than an outside diameter of the needle.

Sides of the slot can further be tapered, such that a width of the slot adjacent to the outer face of the perimeter side wall is greater than a width of the slot adjacent to the inner face of the perimeter side wall. Still further, in one aspect, the width of the slot adjacent to the outer face of the perimeter side wall is greater than the outside diameter of the needle, and the width of the slot adjacent to the inner face of the perimeter side wall is less than the outside diameter of the needle. In one example, the width of the slot adjacent to the outer face of the perimeter side wall is between 0.035-0.037 inches, the width of the slot adjacent to the inner face of the perimeter side wall is between 0.032-0.035 inches, and the outside diameter of the needle is 0.035 inches.

In another aspect, the capture hood is tapered over at least a portion of the distal end thereof. In this aspect, the diameter of the outer face and the inner face of the perimeter side wall decrease to closely house a tip of the needle. In an alternative aspect, the capture hood is cylindrical beginning at the proximal end thereof and longitudinally maintains a consistent internal and external diameter to a location generally adjacent to a distal tip of the needle (i.e., when the assembly is in a post-use position, with movable arm extending parallel to the needle), where the capture hood then tapers with decreasing internal and external diameter to the distal end thereof.

In a further aspect, the capture hood is cylindrical beginning at the proximal end thereof and continues longitudinally with consistent internal and external diameter to a location generally adjacent to a bend in a distal end of the needle (i.e., when the assembly is in a post-use position, with movable arm extending parallel to the needle), where the capture hood then tapers with decreasing internal and external diameter to the distal end thereof. The decreasing diameter of the outer face and the inner face of the perimeter side wall provide a close, snug housing for the tip of the needle.

Other aspects of the present invention include the movable arm having a hinge at the proximal end thereof, where the hinge provides the pivotability of the movable arm relative to the body. In one embodiment, the body is defined as an elbow, where the elbow is movably/pivotably attached to the arm at a pit of the elbow. The body can further includes an extending tube proximally extending from the body, and at least one latch disposed on a first, outer face of the movable arm to clamp the movable arm to the extending tube when the Huber needle assembly with safety capture device is in a pre-use position.

Further aspects include one or more latches disposed on a second, inner face of the movable arm, to clamp the movable arm to the needle when the assembly is in a post-use, needle safety position. The at least one handle (preferably two handles) extend(s) from a distal end of, and is/are integral to, the body. The body and the movable arm can be integrally Formed/molded. The hinge at the proximal end of the movable arm could simply be a crimp in the integrally formed structure.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A is a close-up, side view of a capture hood (nearing a capture position) of the safety capture device of the Huber needle assembly of FIG. 1;

FIG. 2B is a top view of the capture hood of FIGS. 1 and 2A;

FIG. 3 is cross-sectional, perspective view of a Huber needle assembly with safety capture device according to another embodiment of the present invention, where the safety capture device is shown in a clamped, pre-safety or pre-use position;

DETAILED DESCRIPTION

A Huber needle assembly with safety capture device desirably includes a needle safety or restraint mechanism (needle tip block mechanism) which safely retains at least a tip portion of the Huber needle that may contain blood products or medication within a needle impenetrable enclosure to reduce or minimize needle sticks to a medical practitioner. The terms "distal" and "proximal" as used herein, refer respectively to directions closer to and away from the bent-tip, delivery end of the needle.

Figure 1:
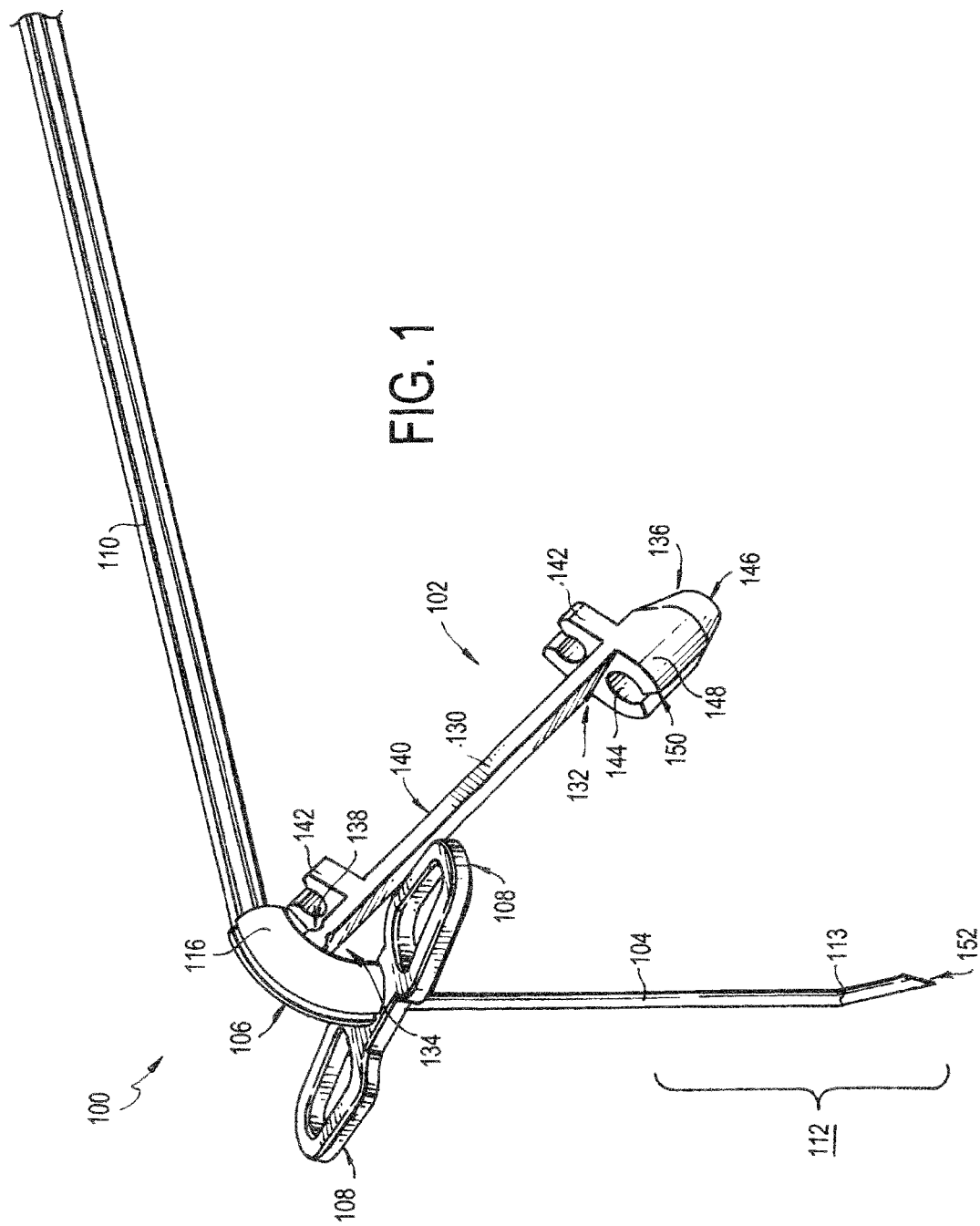
FIG. 1 is a perspective view of a Huber needle assembly with safety capture device according to one embodiment of the present invention, where the safety capture device is shown freely movable about a hinge.

Referring to FIGS. 1-8A, the present invention provides a Huber needle assembly with a safety capture device that substantially minimizes the risk of injury and user exposure to blood borne pathogens, drugs, and any other undesirable articles, living or non-living, that can be transported through the air or by direct contact. As shown in FIG. 1, the Huber needle assembly 100 includes a safety capture device 102, a needle 104, a body 106, a pair of winged handles 108, and an extending tube 110.

The components of the Huber needle assembly 100 can be formed from suitable engineering plastics. In an exemplary embodiment, the body 106, the winged handles 108, and an entirety of the safety capture device 102 (movable arm 130, capture hood 136, etc.), could integrally form a unitary structure. It is to be understood, however, that the individual components could be separate components and connected, either temporarily or permanently, whether mechanically attached adhered, or welded.

The needle 104 is formed of metal, such as stainless steel. The needle can be of one-piece construction, with a 90° bend (curvature) located somewhat midway thereon. A distal end 112 of the needle 104 (distal relative to the 90° bend) includes a bend 113 nearing a distal tip 152, the distal end 112 being longer than a proximal end 114 of the needle 104 (proximal of the 90° bend). The needle 104 is securely mounted within and relative to the body 106.

As shown in FIG. 1, which illustrates one embodiment of the present invention in a perspective view, the body 106 is an elbow 116—in this instance, a substantially 90° elbow. The pair of handles 108 are configured at a distal end of the elbow 116, fixed to or integral with the elbow 116, extending substantially perpendicularly outwardly from the elbow 116. Alternatively, a different body 106 could he employed. For example in FIG. 5, another embodiment of the present invention shows the body 106 as a cylindrical cap 118. The cap 118 can be primarily vertically oriented, and can include a hollow housing 120 (perhaps perpendicularly) extending from the cap 118 to receive a distal end of the extending tube 110. In any embodiment, the needle would undergo a directional transition within the body 106 (likely 90°) to facilitate the use (i.e., the insertion and extraction of the needle 104 during use) of the Huber needle assembly 100. In alternate embodiments, the directional transition occurring in the body 106 may not be necessary, or may include an angle other than 90°.

Referring to FIG. 1, the safety capture device 102 includes, at least, a movable (swinging) arm 130 having a distal end 132 and a proximal end 134. A capture hood 136 is located at the distal end 132 of the movable arm 130, with the body 106 located at the proximal end 134. The body 106 and the arm 130 are joined, with a hinge 138 located thereby, at or near the body 106 (or at the pit of the elbow 116—see also FIG. 3). In an extruded engineering plastic unitary embodiment of the body 106 and the movable arm 130, the hinge 138 may simply be a crimp molded therein.

The movable arm 130 is capable of pivoting about the hinge 138 (i.e., a longitudinal axis of the movable arm 130 pivots (swings) about an axis of the hinge 138—the axis of the hinge 138 being perpendicular to the longitudinal axis of the movable arm 130). Accordingly, the movable arm 130 pivots about the hinge 138 within a range defined between the extending tube 110 and the needle 104. Therefore, the movable arm 130 pivots (swings) about the hinge 138 in a plane defined by and passing through a longitudinal axis of the extending tube 110 and a longitudinal axis of the needle 104.

In this embodiment, disposed about a first (outer) face 140 of the arm 130 are two latches (clamps) 142. The latches 142 clamp the movable arm 130 to the extending tube 110 when the movable arm 130 is in a clamped, pre-safety or pre-use position (as shown in FIG. 3).

Disposed at the distal end 132 of the movable arm 130 is the capture hood (chamber) 136. Referring now to FIGS. 1 and 2, the capture hood 136 is generally cylindrical, having an open proximal end 144 and a closed distal end 146. The distal end 146 can be tapered over a portion of the length of the capture hood 136; for example, narrowing externally and internally to the distal end 146 tip of the capture hood 136. The transition location between capture hood 136 cylindrical shape and taper shape could occur, as shown in FIG. 2A, in a vicinity of the tip 152 of the needle 104 (i.e., when the safety capture device 102 is in, or nearing, a post-use, safety, needle capture position). Alternatively, the transition location could occur more proximally, for example, in a vicinity of the bend 113 of the needle 104. The tip of the distal end 146 of the capture hood 136 could alternatively be open.

The capture hood 136 has a perimeter side wall 148 with a slot 150 therethrough, the slot 150 extending over all, most, or at least a portion of the length (height) of the capture hood 136. In the embodiment of the capture hood 136 of the safety capture device 102 shown in FIGS. 1 through 6, it is preferable that a longitudinal center line of the slot 150 be aligned with the longitudinal axis of the needle 104. Further, it is preferable that the bend 113 in the distal end 112 of the needle 104 occur so that the longitudinal axis of the needle 104, including the longitudinal axis of the bent, distal end 112 portion, remain aligned with 9 and on the plane defined by the longitudinal axis of the extending tube 110 and the longitudinal axis of the needle 104. Accordingly, the tip 152 of the needle 104 would enter the slot 150 of the capture hood 136 along the longitudinal center line of the slot 150, and the tip 152 of the needle 104 would enter the slot 150 prior to any remainder of the needle 104 entering the slot 150. Further, an entirety of a portion of the distal end 112 of the needle 104 entering the slot 150 (i.e., both bent-tip and straight portions) of the needle 104) would have an entirety of its respective longitudinal axis aligned with the center line of the slot 150 when entering.

In one aspect of the invention, the capture hood 136 is configured in length to receive at least a tip 152 of the needle 104. Preferably, and usually, at least a portion of the distal end 112 of the needle 104 is additionally captured in the capture hood 136. Alternatively, the capture hood 136 could be elongated to receive a totality of the distal end 112 of the needle 104. Preferably, a totality of the needle 104 would not be received in the capture hood 136; but if desired, such an embodiment is contemplated.

Referring now to FIG. 2B, which is a top view of the capture hood 136 (looking distally (down) the movable arm 130 into the open, proximal end 144 of the capture hood 136), it can be seen that the slot 150 has an inner width (IW) that is less than a respective outer width (OW) of the slot 150. That is, in this embodiment, the slot 150 opening between the edges of an inner perimeter of the side wall 148 is less than the slot 150 opening between the edges of an outer perimeter of the side wall 148. In this embodiment, the sidewalls of the slot are therefore tapered narrowing inwardly.

Preferably, in this FIG. 2B embodiment, the inner width (IW) of the slot 150 is a dimension slightly less than a dimension of the outer diameter (OD) of the needle 104, with the outer width (OW) of the slot 150 being a dimension slightly greater than a dimension of the outer diameter (OD) of the needle 104. Accordingly, the needle 104 encounters slight resistance when entering the capture hood 136 (i.e., when passing through (i.e., transversing) the slot 150), and cannot transversely exit an interior portion of the capture hood 136 without human intervention.

For example, when used with a 0.035 inch outer diameter (OD) needle 104, the inner width (LW) of the slot 150 may be 0.032-0.035 inches, and the outer width (OW) of the slot 150 may be 0.035 0.037 inches. In an alternative embodiment, the inner width (LW) and the outer width (OW) of the slot 150 may both be between 0.032-0.035 inches. As such, other embodiments of the present invention may include inner widths (IW) of the slot 150 ranging in dimension from slightly less than, equal to, or slightly greater than, the outer width (OW) of the slot 150, and/or the outer diameter (OD) of the needle 104. In other words, the sidewalls of the slot can be tapered narrowing inwardly, straight, or tapered narrowing outwardly. Normally, at least one of the inner width (LW) and/or outer width (OW) of the slot 150 is slightly less than or equal to the outer diameter (OD) of the needle 104. In any case, the dimensions of the inner width (LW) and the outer width (OW) of the slot 150 may be selected so that the needle 104 encounters slight resistance when transversing (passing through) the slot 150 into the capture hood 136, and cannot exit the capture hood 136 without human intervention. As shown in FIG. 2, when the tip 152 of the needle 104 (and at least a portion of the distal end 112) is captured in the chamber 136, a second (inner) face 154 of the movable arm is generally adjacent to and parallel to the needle 104.

When the movable arm 130 is in the clamped, pre-safety or pre-use position (as shown in FIG. 3), the movable arm 130 is latched to the extending tube 110 via the one or more clamps 142. When the user is ready to swing the movable arm 130 toward a capture position, the clamps 142 are released from the extending tube 110, and the movable arm 130 pivots about the hinge 138 towards the needle 104. At least a tip 152 of the needle 104 (and usually at least a portion of, or a totality of, the distal end 112 of the needle 104) is captured in the chamber 136 upon a passing of the needle 104 through the slot 150. The tip 152 of the needle 104 is prevented from exiting the chamber (capture hood) 136 by the side wall 148, and by at least an inner width (LW) of the slot 150 being of a dimension less than the outer diameter (OD) of the needle 104.

In another embodiment of the Huber needle assembly 100 with safety capture device 102, as shown in FIG. 3, the movable arm 130 includes, on the second, inner face 154 thereof, a latch 142 having two, offset clamping arms 142A, 142B. The two clamping arms 142A, 142B provide an additional securing mechanism for the safety capture device 102 when the movable arm 130 is in a captured, in-use, safety position (i.e., where at least the tip 152 of the needle 104 is captured in chamber 136 (not shown in FIG. 3), In the captured, in-use, safety position, the latch 142 having two, offset clamping arms 142A, 142B, engages the needle 104, further securing the movable arm 130. In other embodiments, more than one latch 142, or latch(es) having varying clamping arm positions, may be employed on either the first, outer face 140, or the second, inner face 154, of the movable arm 130.

Figure 4:
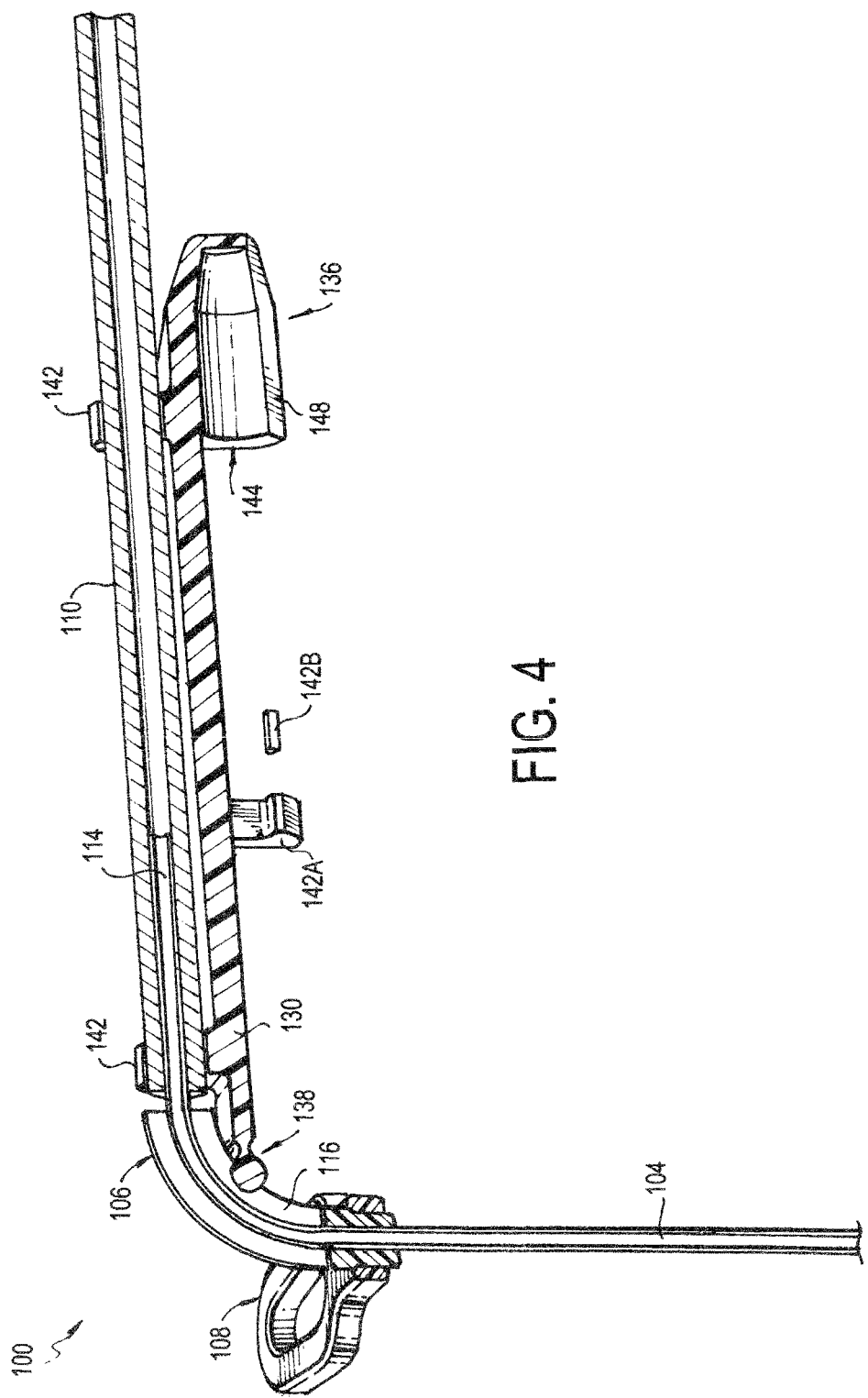
FIG. 4 is a further internal, cross-section view of the Huber needle assembly with safety capture device shown in FIG. 3, where the cross-section is taken midway through a needle, elbow and extending tube thereof.

FIG. 4 illustrates the embodiment of the Huber needle assembly 100 having a safety capture device 102, shown in FIG. 3, but FIG. 4 has a differing cross-section—taken midway through the needle 104, elbow 116 and extending tube 110. FIG. 4 therefore provides a detailed view of the 90° transition of the needle through body 106, and provides in detail the extending tube 110 over needle 104 connection on the proximal side of the body 106 of this embodiment.

Figure 5:
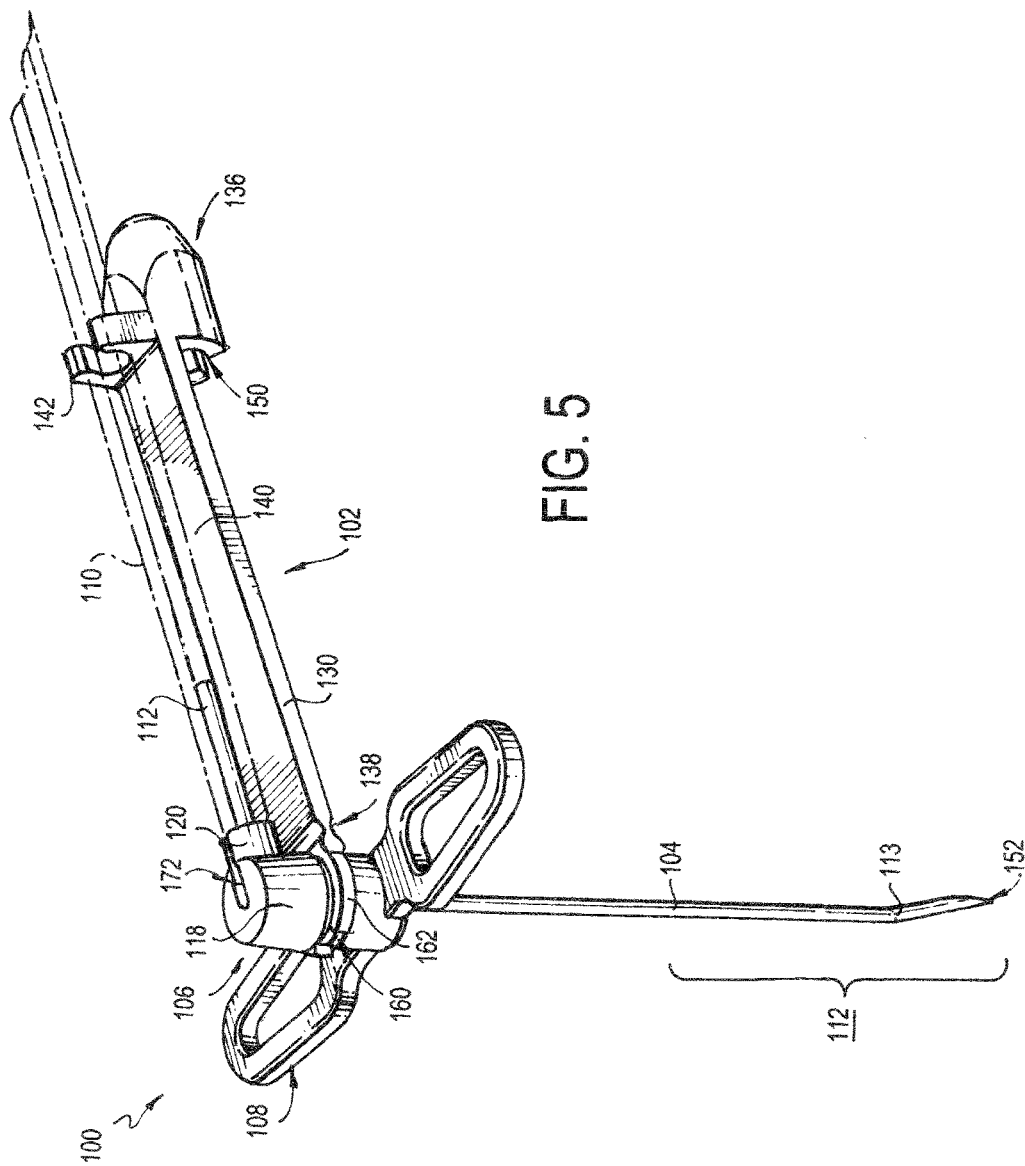
FIG. 5 is a perspective view of a Huber needle assembly with safety capture device according to a further embodiment of the present invention, where the safety capture device is shown in a clamped, pre-safety or pre-use position.

FIG. 5 illustrates a further embodiment of the present invention, where the Huber needle assembly 100 having a safety capture device 102 includes a body 106 formed as a cylindrical cap 118. The cylindrical cap 118 can be primarily vertically oriented (i.e., longitudinally oriented relative to the extending needle 104). In this embodiment, the hollow housing 120 extends substantially perpendicularly to the cylindrical cap 118 and receives therein a distal end of the extending tube 110. In this embodiment, the cylindrical cap 118 includes a groove 160 transversing (relative to a longitudinal axis of the cylindrical cap 118) a perimeter thereof. The transverse groove 160 houses (and provides a connection point to) a horseshoe collar 162, located at the proximal end 134 of the movable arm 130. The horseshoe collar 162 can be fixedly (e.g., adhered/welded) or removably joined (snap fit) to and within the groove 160. Again, the movable arm 130 is capable of pivoting (swinging) about the hinge 138, movable along a plane defined by and through the longitudinal axes of the extending tube 110 and the needle 104. The attachment (whether fixed or removably joined) between the horseshoe collar 162 and the groove 160 could include a further mechanical securement to ensure a lack of movement of the horseshoe collar 162 relative to the groove 160 during a pivoting of the movable arm 130 about the hinge 138, to further ensure that the movable arm 130 pivots (swings) only along the plane defined by and through the longitudinal axes of the extending tube 110 and the needle 104.

Figure 6:
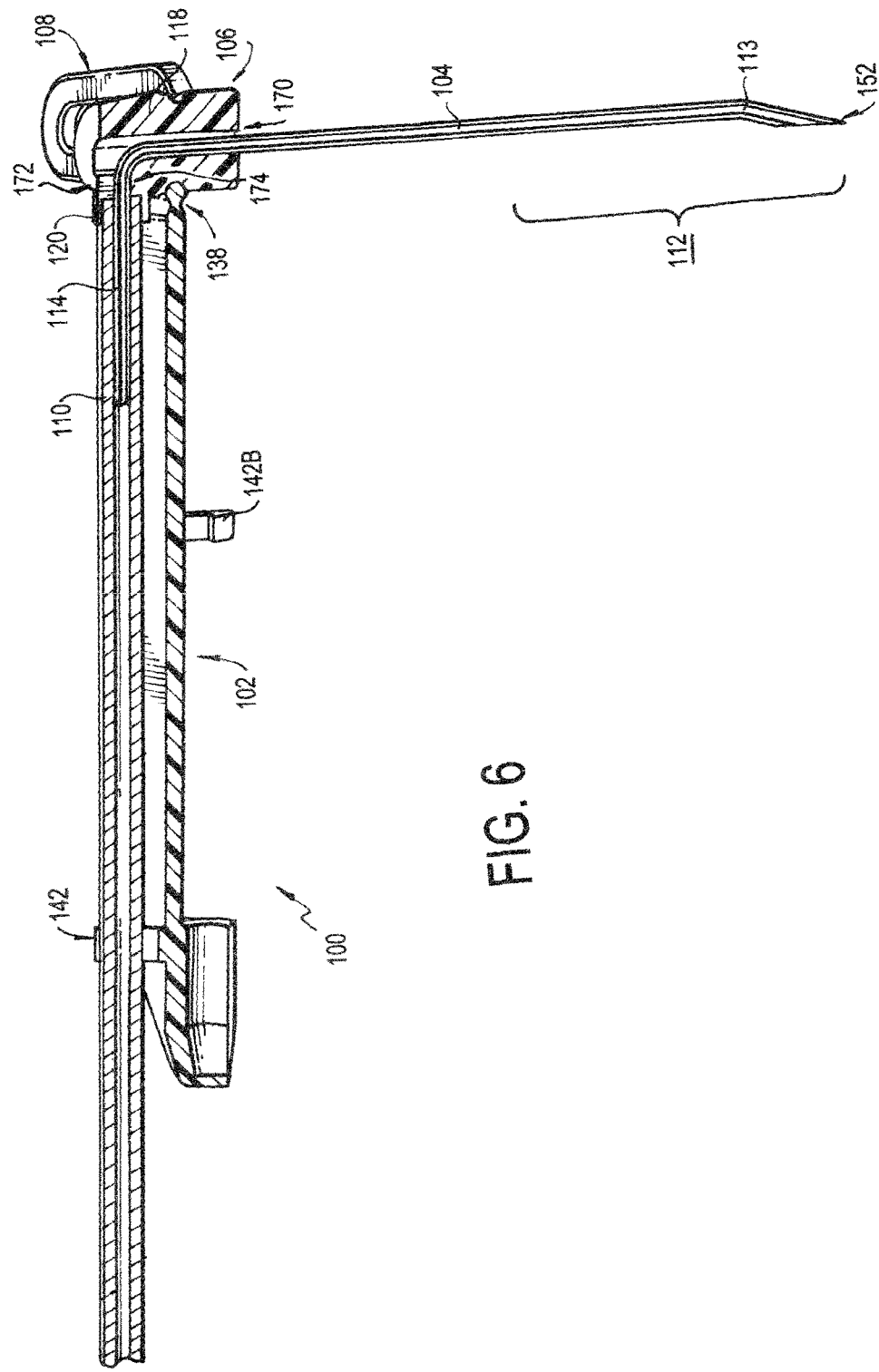
FIG. 6 is a rear side, cross-sectional view of the Huber needle assembly with safety capture device shown in FIG. 5.
Figure 7:
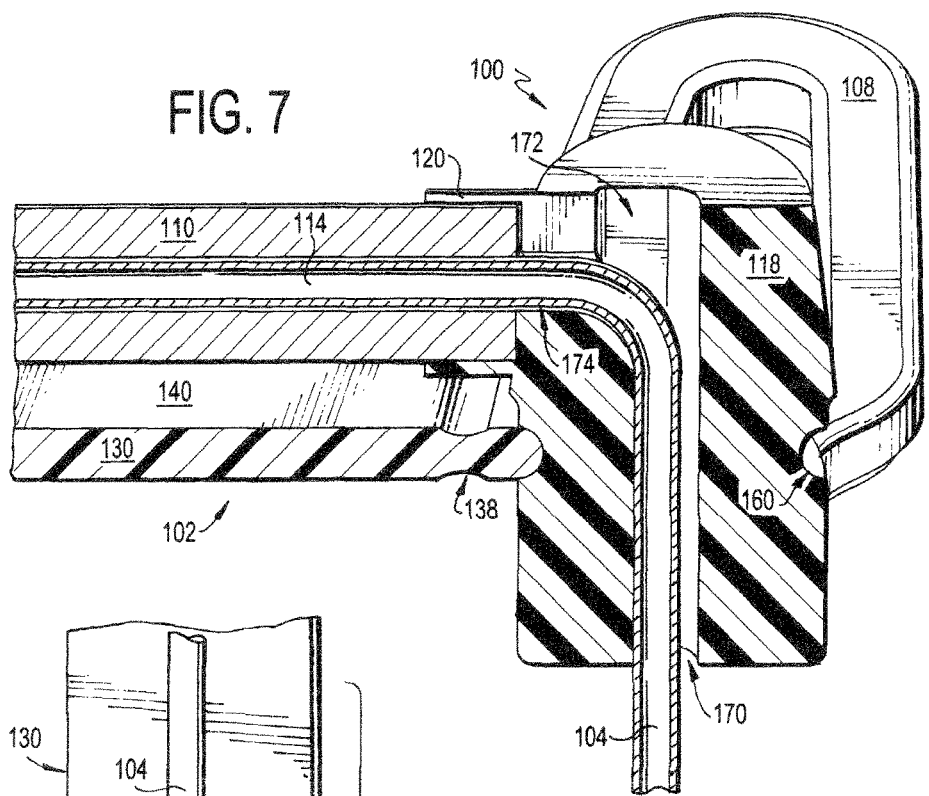
FIG. 7 is a close-up of the view of the Huber needle assembly with safety capture device shown in FIG. 6.

FIG. 6 illustrates a rear-side cross-sectional view of the FIG. 5 embodiment of the present invention, where the Huber needle assembly 100 with safety capture device 102 involves a body 106 formed as a cylindrical cap 118. FIG. 7 is a close-up of FIG. 6. The FIGS. 6 and 7 cross-sectional views show an internal, longitudinal (vertical) needle bore 170 within the cap 118, the internal needle bore 170 providing for the distal extension of the needle 104 therefrom. Also shown is an open channel 172, horizontally oriented relative to the needle bore 170, the open channel 172 extending through the hollow housing 120 and into the cap 118, where a bottom 174 of the channel 172 provides a housing base for the needle 104. During assembly, the one-piece needle 104 with 90° bend is first placed into the open channel 172 with the distal end 112 with bent tip portion (beginning at bend 113) of the needle 104 inserted through the needle bore 170. The proximal end 114 (proximal to the 90° bend) of the needle 104, extending proximally from the body 106 (and extending from a central, longitudinal axis of the hollow housing 120) is connected (frictionally fit within) the extending tube 110. The extending tube 110 is then further frictionally connected to and within the hollow housing 120. The extending tube 110 to hollow housing 120 connection is then suitably bonded. The proximal end 114 of needle 104 to extending tube 110 connection, together with the extending tube 110 to hollow housing 120 connection, provide for, resist, and protect the Huber needle assembly 100 (and the respective components and connections thereof) from the many possible destructive forces resulting from use (i.e., forces occurring during needle insertion into, and needle withdrawal from, a subcutaneous access port device). Any and all frictional connections can be further adhered/welded if applicable and as desired.

Figure 8A:
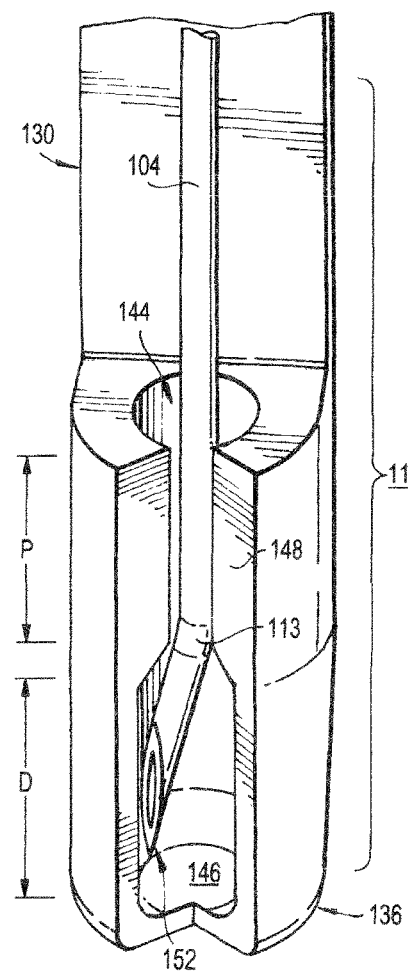
FIG. 8A is a close-up view of a capture hood according to another embodiment of the present invention, where the capture hood secures a needle in a capture position.

FIG. 8A illustrates another embodiment of a capture hood 136 of the present invention. In this view, the needle 104 is shown in a post-use, safety capture position within the chamber. In one aspect, this embodiment of the capture hood 136 could be employed where the bend 113 in the distal end 112 of the needle 104 is off-plane (i.e., the longitudinal axis of the bent, distal end 112 portion of the needle 104 is not aligned with and along the plane defined by and through the longitudinal axis of the remaining needle 104 and the longitudinal axis of the extending tube 110—i.e., the plane of swing of the movable arm 130). In this aspect, an inner width (IW) and an outer width (OW) of the slot 150 may, over at least a distal portion of the length of the slot 150, require wider dimensioning to accommodate and receive an off-plane, bent-tip distal end 112 of the needle 104.

In the FIG. 8A embodiment, the capture hood 136 is generally cylindrical, having an open proximal end 144 and a closed distal end 146. The capture hood 136 has a perimeter side wall 148 with a slot 150 therethrough, the slot 150 extending over all, most, or at least a portion of the length (height) of the capture hood 136.

In the FIG. 8A embodiment, a longitudinal center line of the slot 150 is aligned with the longitudinal axis of the needle 104. In this embodiment, however, and as shown, the slot 150 is wide enough to accommodate a needle 104 having an off-plane bend 113 in the distal end 112 thereof. Over a proximal portion (P) of the slot 150 length, a thickness of the sidewall 148, and the dimensions of the inner width (IW) and the outer width (OW) of the slot 150 may be similar to that of the prior capture hood 136 embodiment. Over a distal portion (D) of the slot 150 length, in the FIG. 8A embodiment, the sidewall 148 thickness is considerably less than that of the proximal portion (P) of the slot 150 length, so to provide a greater inner width (IW) dimension—capable of receiving therein an off-plane, bent-tip distal end 112 of the needle 104. In other embodiments, a longitudinal center line of the slot 150 is not aligned with the longitudinal axis of the needle 104.

Figure 8B:
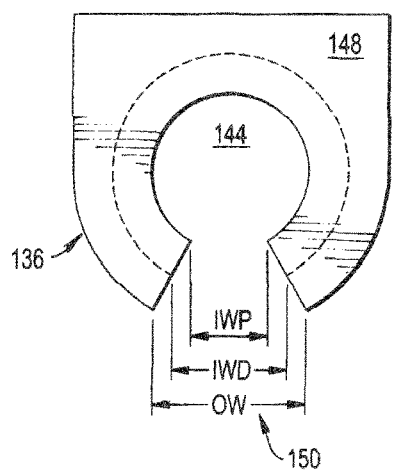
FIG. 8B is a top view of the capture hood of FIG. 8A.

FIG. 8B is a top view of the capture hood 136 of FIG. 8A (looking distally (down) the movable arm 130 into the open, proximal end 144 of the capture hood 136). Here, it can be seen that the slot 150 has an inner width (IWP) over the proximal portion (P) of the slot 150 length, and an inner width (IWD) over distal portion (D) of the slot 150 length (shown in dotted lines), that is less than a respective outer width (OW) of the slot 150. Again, the sidewalls of the slot 150 are tapered (here—tapered narrowing inwardly).

In this FIG. 8A embodiment, the slot 150 opening between the edges of an inner perimeter of the side wall 148 is less than the slot 150 opening between the edges of an outer perimeter of the side wall 148. Preferably, in this embodiment, the inner width (IWP) over the proximal portion (P) of the slot 150 length is a dimension slightly less than a dimension of the outer diameter (OD) of the needle 104, with the outer width (OW) of the slot 150 being a dimension slightly greater than a dimension of the outer diameter (OD) of the needle 104. Accordingly, the needle 104 encounters slight resistance when entering the capture hood 136 (i.e., when passing through (i.e., transversing) the slot 150), and cannot transversely exit an interior portion of the capture hood 136 without human intervention. In this embodiment, the inner width (IWD) over the distal portion (D) of the slot 150 length could be one (1) to four (4) times greater than the outer diameter (OD) of the needle 104. More preferably, the inner width (IWD) over the distal portion (D) of the slot 150 length might be two (2) to three (3) times greater than the outer diameter (OD) of the needle 104.

In this embodiment, the inner width (IWP) over the proximal portion (P) of the slot 150 length differs from the inner width (IWD) over distal portion (D) of the slot 150 length due to differing sidewall 148 thicknesses over the proximal (P) and the distal (D) portions of the slot 150 length (i.e., the outer width (OW) of the slot 150 is of constant dimension over the proximal (P) and the distal (D) portions of the slot 150 length). In other embodiments, the sidewall 148 thickness could remain constant over the proximal (P) and the distal (D) portions of the slot 150 length, and the outer width (OW), the inner width (IWP) of the proximal portion (P), and the inner width (IWD) of the distal portion (D), of the slot 150 length, could vary to obtain the desired, respective dimensions.

In the FIG. 8A embodiment, a transition portion is located between the proximal (P) and the distal (D) portions of the slot 150 length, where the sidewall 148 thickness transitions between that necessary to obtain the respective inner width (IWP) of the proximal portion (P) and that for the respective inner width (IWD) of the distal portion (D) of the slot 150 length.

This sidewall 148 thickness transition portion could occur, as shown in FIG. 8A, in a vicinity 17 of the bend 113 in the distal end 112 of the needle 104 (when the safety capture device 102 is in a post-use, safety, needle capture position). Alternatively, the sidewall 148 thickness transition portion could occur more proximally. The distal end 146 of the capture hood 136 in this embodiment could alternatively be open.

In use, after Huber needle injection or infusion is complete, a medical practitioner unclamps the latches 142, allowing the movable arm 130 to separate from extending tube 110 and freely pivot about the hinge 138. The medical practitioner then carefully withdraws the needle 104 from a patient by gently pulling on the pair of winged handles 108. When the needle 104 exits the skin of the patient, the movable arm 130 pivots (or has pivoted) to a position allowing at least the tip 152 of the needle 104 (and, depending on the embodiment, a portion of the distal end 112 of the needle 104) to frictionally pass through the slot 150 and into the capture hood 136. With a slight pinch of the needle 104 into the slot 150, the needle 104 overcomes the frictional force resulting from a width of the slot 150 being less than the outside diameter of the needle 104, thereby capturing and securing the needle 104 in the chamber (capture hood) 136. The Huber needle assembly 100 with safety capture device 102 can then be safely disposed. Because the tip 152 of the needle 104 (and a portion of the distal end 112 of the needle 104) is within the capture hood 136 of the needle capture assembly 102, the Huber needle assembly 100 minimizes the risk of accidental needle stick to a medical practitioner (user) or to a patient. The Huber needle assembly 100 also minimizes any risk of inhaling any emissions arising from a substance traveling through the needle 104.

In the depicted embodiments, the needle 104 includes a rounded portion within the respective body 106 that conforms to a substantially 90° elbow to facilitate the inserting and extracting of the needle 104 during use. In alternate embodiments, the needle 104 may lack this bent portion within the body 106, have several bent portions, or have a bent portion that is not a substantially 90° elbow. The depicted needle 104 also has a substantially circular cross-sectional shape, but in alternate embodiments, the needle 104 can have a cross-sectional shape that is oval-like, triangular, rectangular, polygonal, or combinations of the aforementioned.

The safety capture device 102 assembly can be adapted to the Huber needle assembly 100 before use by the user (i.e., the safety capture device 102 could be manufactured and provided separately from the Huber needle assembly 100, and placed thereon just prior to use). Or, the safety capture device 102 could be a separate component but provided together with the Huber needle assembly 100 in a kit. For example, just prior to use, the horseshoe collar 162 would be friction fit into the transverse groove 160 of the cylindrical cap 118. Preferably, the safety capture device 102 is incorporated into the Huber needle assembly 100 during manufacturer, perhaps as a unitary structure.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. Specific dimensions of any particular embodiment are described for illustration purposes only. It should therefore be understood that this invention is not limited to the particular embodiments described herein, but is intended to include all changes and modifications that are within the scope and spirit of the invention.

What is claimed is:

1. A Huber needle assembly with safety capture device, comprising:
    a body;
    a needle distally extending from the body;
    at least one handle fixed relative to the needle and the body;
    a movable arm having distal and proximal ends, the movable arm capable of pivoting relative to the body;
    a capture hood residing at the distal end of the movable arm, the capture hood being generally cylindrical about a longitudinal axis thereof and further defined by:
        a perimeter side wall about the longitudinal axis, the perimeter side wall having an outer face and an inner face relative to the longitudinal axis;
        an open proximal end; and
        a slot through the perimeter side wall, the slot having a depth defined by a thickness of the side wall between the outer face and the inner face of the side wall, the slot having two sides, each characterized by an edge along the depth defined by the thickness of the side wall between the outer face and the inner face of the side wall, the slot providing access into an internal cylindrical chamber of the capture hood defined in part by the perimeter side wall, the slot extending longitudinally over at least a portion of a length of the capture hood to the open proximal end of the capture hood, at least a portion of the slot having a width less than an outside diameter of the needle;
    an extending tube proximally extending from the body;
    at least one latch disposed on a first, outer face of the movable arm to clamp the movable arm to the extending tube when the assembly is in a pre-use position.

2. The assembly of claim 1, wherein at least a portion of the sides of the slot are tapered such that a width of at least a portion of the slot adjacent to the outer face of the perimeter side wall is greater than a width of at least a portion of the slot adjacent to the inner face of the perimeter side wall.

3. The assembly of claim 2, wherein the width of at least a portion of the slot adjacent to the outer face of the perimeter side wall is greater than the outside diameter of the needle, and the width of at least a portion of the slot adjacent to the inner face of the perimeter side wall is less than the outside diameter of the needle.

4. The assembly of claim 3, wherein the width of at least a portion of the slot adjacent to the outer face of the perimeter side wall is between 0.035-0.037 inches, the width of at least a portion of the slot adjacent to the inner face of the perimeter side wall is between 0.032-0.035 inches, and the outside diameter of the needle is 0.035 inches.

5. The assembly of claim 1, wherein a distal end of the capture hood is closed.

6. The assembly of claim 1, wherein the capture hood is tapered over at least a portion of a distal end thereof, wherein a diameter of the outer face of the perimeter side wall and a diameter of the inner face of the perimeter side wall both decrease to closely house a tip of the needle.

7. The assembly of claim 1, wherein the capture hood is cylindrical beginning at a proximal end thereof and continuing to a location generally adjacent to a tip of the needle when the assembly is in a post-use, safety-capture position, the capture hood then tapering to a distal end thereof.

8. The assembly of claim 1, wherein the capture hood is cylindrical beginning at a proximal end thereof and continuing to a location generally adjacent to a bend in a distal end of the needle, when the assembly is in a post-use, safety-capture position, the capture hood then tapering to a distal end thereof, wherein a diameter of the outer face of the perimeter side wall and a diameter of the inner face of the perimeter side wall both decrease to closely house a tip of the needle.

9. The assembly of claim 1, wherein the movable arm consists of a single hinge, the single hinge located at the proximal end of the movable arm, the single hinge providing pivotability of the movable arm relative to the body.

10. The assembly of claim 9, where the body is defined as an elbow, the elbow being movably attached to the movable arm at a pit of the elbow.

11. The assembly of claim 9, wherein a longitudinal axis of the movable arm pivots about a longitudinal axis of the single hinge, the longitudinal axis of the movable arm being perpendicular to the longitudinal axis of the single hinge.

12. The assembly of claim 9, wherein the body and the moveable arm are integrally molded, and the single hinge at the proximal end of the moveable arm is a crimp therein.

13. The assembly of claim 1, further comprising at least one latch disposed on a second, inner face of the movable arm to clamp the movable arm to the needle when the assembly is in a post-use, safety capture position.

14. The assembly of claim 1, wherein the at least one handle extends from a distal end of, and is integral to, the body.

15. The assembly of claim 1, where the slot has a distal portion and a proximal portion, and wherein the depth of the proximal portion of the slot is greater than the depth of the distal portion of the slot.

16. The assembly of claim 15, wherein the slot is tapered narrowing inwardly.

17. The assembly of claim 15, wherein the sides of the proximal portion of the slot are tapered such that a width of the proximal portion of the slot adjacent to the outer face of the perimeter side wall is greater than a width of the proximal portion of the slot adjacent to the inner face of the perimeter side wall.

18. The assembly of claim 17, wherein the width of the proximal portion of the slot adjacent to the outer face of the perimeter side wall is greater than the outside diameter of the needle, and the width of the proximal portion of the slot adjacent to the inner face of the perimeter side wall is less than the outside diameter of the needle.

19. The assembly of claim 18, wherein the width of the proximal portion of the slot adjacent to the outer face of the perimeter side wall is between 0.035-0.037 inches, the width of the proximal portion of the slot adjacent to the inner face of the perimeter side wall is between 0.032-0.035 inches, and the outside diameter of the needle is 0.035 inches.

20. The assembly of claim 15, wherein the sides of the distal portion of the slot are tapered such that a width of the distal portion of the slot adjacent to the outer face of the perimeter side wall is greater than a width of the distal portion of the slot adjacent to the inner face of the perimeter side wall.

21. The assembly of claim 20, wherein the width of the distal portion of the slot adjacent to the outer and to the inner faces of the perimeter side wall is greater than or equal to 2.5 times the outside diameter of the needle.

22. The assembly of claim 21, wherein the width of the distal portion of the slot adjacent to the outer and to the inner faces of the perimeter side wall is greater than or equal to 0.0875 inches, and the outside diameter of the needle is 0.035 inches.

23. A Huber needle assembly with safety capture device, comprising:
  a body;
  a needle distally extending from the body, the needle comprising a proximal end and a distal end defining a longitudinal axis of the needle;
  at least one handle fixed relative to the needle and the body;
  a movable arm having distal end and a proximal end defining a longitudinal axis of the movable arm, the movable arm capable of pivoting relative to the body about a hinge;
  a capture hood residing at the distal end of the movable arm, the capture hood comprising a slot providing access into the capture hood;
  an extending tube extending from the body, a length of the extending tube defining a longitudinal axis of the extending tube;
  at least one latch disposed on a first, outer face of the movable arm to clamp the movable arm to the extending tube when the assembly is in a pre-use position; and,
  wherein the movable arm pivots about the hinge in a plane defined by the longitudinal axis of the extending tube and the longitudinal axis of the needle so that the movable arm extends parallel to the needle in a first position and the movable arm extends parallel to the extending tube in a second position.

24. The assembly of claim 23, wherein the second position causes the needle to insert laterally into a chamber of the capture hood via the slot.

* * * * *